(12) United States Patent
Kristoffersen et al.

(10) Patent No.: US 12,390,189 B2
(45) Date of Patent: Aug. 19, 2025

(54) METHODS AND SYSTEMS FOR ULTRASOUND IMAGING WITH PULSE-INVERSION SCHEME AND RETROSPECTIVE TRANSMIT TECHNIQUES

(71) Applicant: GE Precision Healthcare LLC, Waukesha, WI (US)

(72) Inventors: Kjell Kristoffersen, Oslo (NO); Anders Sørnes, Oslo (NO); Bastien Denarie, Nesøya (NO)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 96 days.

(21) Appl. No.: 17/236,930

(22) Filed: Apr. 21, 2021

(65) Prior Publication Data
US 2022/0338835 A1    Oct. 27, 2022

(51) Int. Cl.
*A61B 8/00* (2006.01)
*A61B 8/14* (2006.01)
*G06T 11/00* (2006.01)
*A61B 8/15* (2006.01)

(52) U.S. Cl.
CPC ............ *A61B 8/145* (2013.01); *A61B 8/5207* (2013.01); *A61B 8/5246* (2013.01); *A61B 8/5253* (2013.01); *G06T 11/006* (2013.01); *A61B 8/15* (2013.01); *A61B 8/52* (2013.01); *G06T 2210/41* (2013.01)

(58) Field of Classification Search
CPC ..... A61B 8/145; A61B 8/5207; A61B 8/5246; A61B 8/4472; A61B 8/485; A61B 8/486; A61B 8/488; A61B 8/0883; A61B 8/5284; A61B 8/5215; A61B 8/5253; A61B 8/15; A61B 8/52; G06T 11/006; G06T 2210/41; G01S 7/52093; G01S 7/52092

See application file for complete search history.

(56) References Cited

U.S. PATENT DOCUMENTS

| | | | |
|---|---|---|---|
| 6,186,950 B1* | 2/2001 | Averkiou | A61B 8/13 600/443 |
| 6,436,046 B1* | 8/2002 | Napolitano | G01S 7/52085 600/458 |
| 6,602,195 B1* | 8/2003 | Krishnan | G01S 7/52085 600/447 |
| 6,682,482 B1* | 1/2004 | Krishnan | G01S 7/52039 600/443 |
| 6,685,641 B2* | 2/2004 | Liu | G01S 7/52028 600/443 |
| 7,833,163 B2* | 11/2010 | Cai | G01S 7/52047 600/447 |
| 8,241,216 B2* | 8/2012 | Loftman | G01S 7/5209 600/443 |
| 9,198,636 B2* | 12/2015 | Napolitano | A61B 8/145 |
| 9,310,475 B2 | 4/2016 | Steinbacher et al. | |
| 9,366,753 B2* | 6/2016 | Hoctor | G01S 7/52085 |

(Continued)

FOREIGN PATENT DOCUMENTS

WO    WO-2018061025 A1 *    4/2018    ......... G01S 15/8915

*Primary Examiner* — Joel Lamprecht
*Assistant Examiner* — James F McDonald, III
(74) *Attorney, Agent, or Firm* — McCoy Russell LLP

(57) ABSTRACT

Various methods and systems are provided an ultrasound device. In one example, a method for ultrasound imaging comprises alternating positive and negative polarity transmits fired from an ultrasound probe at different locations.

15 Claims, 5 Drawing Sheets

Location / Steer angle

(56) References Cited

U.S. PATENT DOCUMENTS

| | | | |
|---|---|---|---|
| 9,883,852 B2* | 2/2018 | Doherty | G16H 50/30 |
| 2005/0131298 A1* | 6/2005 | Cai | G01S 15/8925 |
| | | | 600/447 |
| 2010/0217124 A1* | 8/2010 | Cooley | G01S 15/8954 |
| | | | 600/443 |
| 2012/0209120 A1* | 8/2012 | Petersen | H03K 5/04 |
| | | | 600/459 |
| 2013/0079639 A1* | 3/2013 | Hoctor | G01S 7/52025 |
| | | | 600/447 |
| 2013/0137986 A1* | 5/2013 | Takeda | G01S 15/8963 |
| | | | 600/447 |
| 2013/0253325 A1* | 9/2013 | Call | A61B 8/5246 |
| | | | 600/447 |
| 2014/0050048 A1* | 2/2014 | Jensen | G01S 15/8977 |
| | | | 367/7 |
| 2014/0276049 A1* | 9/2014 | Doherty | G01S 7/52042 |
| | | | 600/438 |
| 2015/0049578 A1* | 2/2015 | Hoctor | G01S 7/52046 |
| | | | 367/7 |
| 2015/0366542 A1* | 12/2015 | Brown | G01S 15/8956 |
| | | | 600/447 |
| 2016/0296204 A1* | 10/2016 | Park | G01S 7/5202 |
| 2018/0038947 A1* | 2/2018 | Zwirn | G01S 7/52077 |
| 2018/0088220 A1* | 3/2018 | Flynn | G01S 15/8997 |
| 2019/0209139 A1* | 7/2019 | Petersen | A61B 8/52 |
| 2019/0235076 A1* | 8/2019 | Angelsen | G01S 15/8913 |
| 2021/0080572 A1* | 3/2021 | Van Rens | G01S 7/52026 |

* cited by examiner

FIG. 9
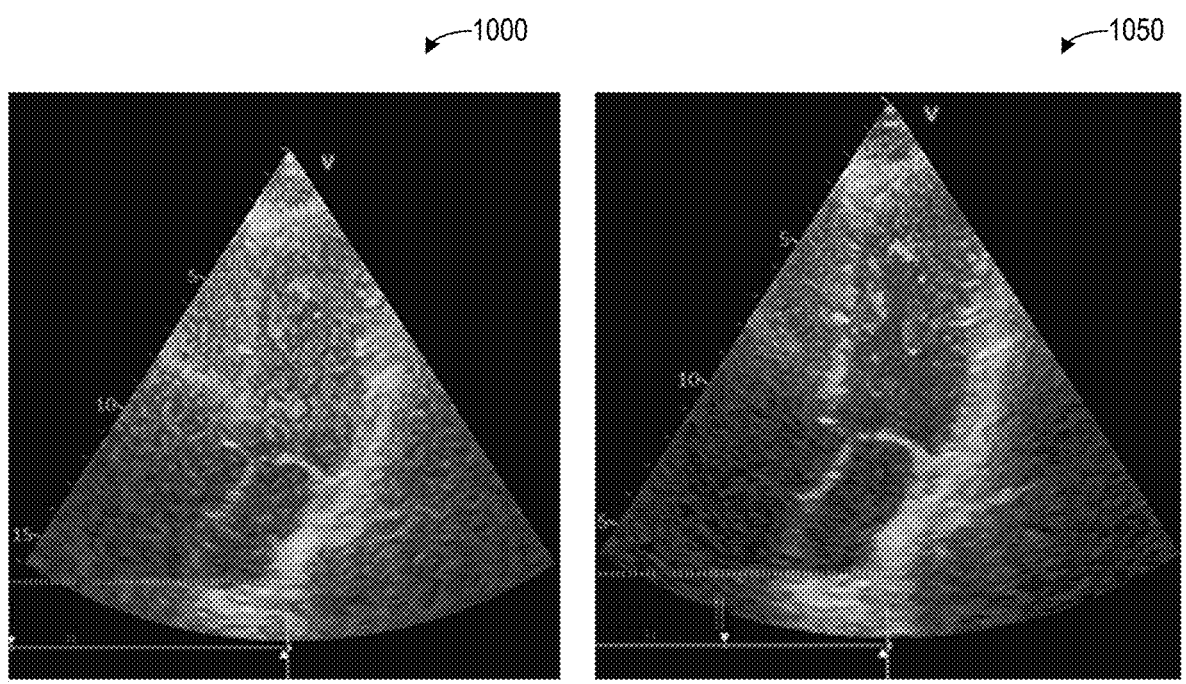
FIG. 10A  FIG. 10B

METHODS AND SYSTEMS FOR ULTRASOUND IMAGING WITH PULSE-INVERSION SCHEME AND RETROSPECTIVE TRANSMIT TECHNIQUES

FIELD

Embodiments of the subject matter disclosed herein relate to retrospective transmit beamforming for an ultrasound system.

BACKGROUND

Diagnostic medical imaging system may include a scan portion and a control portion having a display. For example, ultrasound imaging systems may include scanning devices such as ultrasound probes connected to an ultrasound system configured to control an acquisition.

Different beamforming techniques may be used to synthetically modify an effective transmit beam used by the ultrasound system to generate an image. For example, retrospective transmit beamforming (RTB) may be used to form a synthetically focused ultrasound image using, standard, scanned, and focused ultrasound transmissions. More particularly, RTB may include a synthetic focus technique that uses standard, scanned-beam transmit data, dynamic receive focusing, and a combination of time-aligned data from multiple transmits to form images.

One variation of an ultrasound system may include a dynamically focused, multi-line acquisition (MLA) beamformer, which may produce multiple receive beamformed output signals for each transmit. This may allow the system a broad transmit beam to be used to illuminate a reflectivity distribution, while more than one narrow receive beam may be used to produce data for image generation. RTB may be used in combination with MLA.

BRIEF DESCRIPTION

In one embodiment, a method for ultrasound imaging comprises transmitting only a first beam with a first waveform at a first location and only a second beam with a second waveform at a second location via an ultrasound probe, wherein the second location is different from the first location and the second waveform is the inverse of the first.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 9 shows an example image according to the first embodiment.

FIGS. 10A and 10B show an example of an image gathered under different conditions.

DETAILED DESCRIPTION

Figure 1:
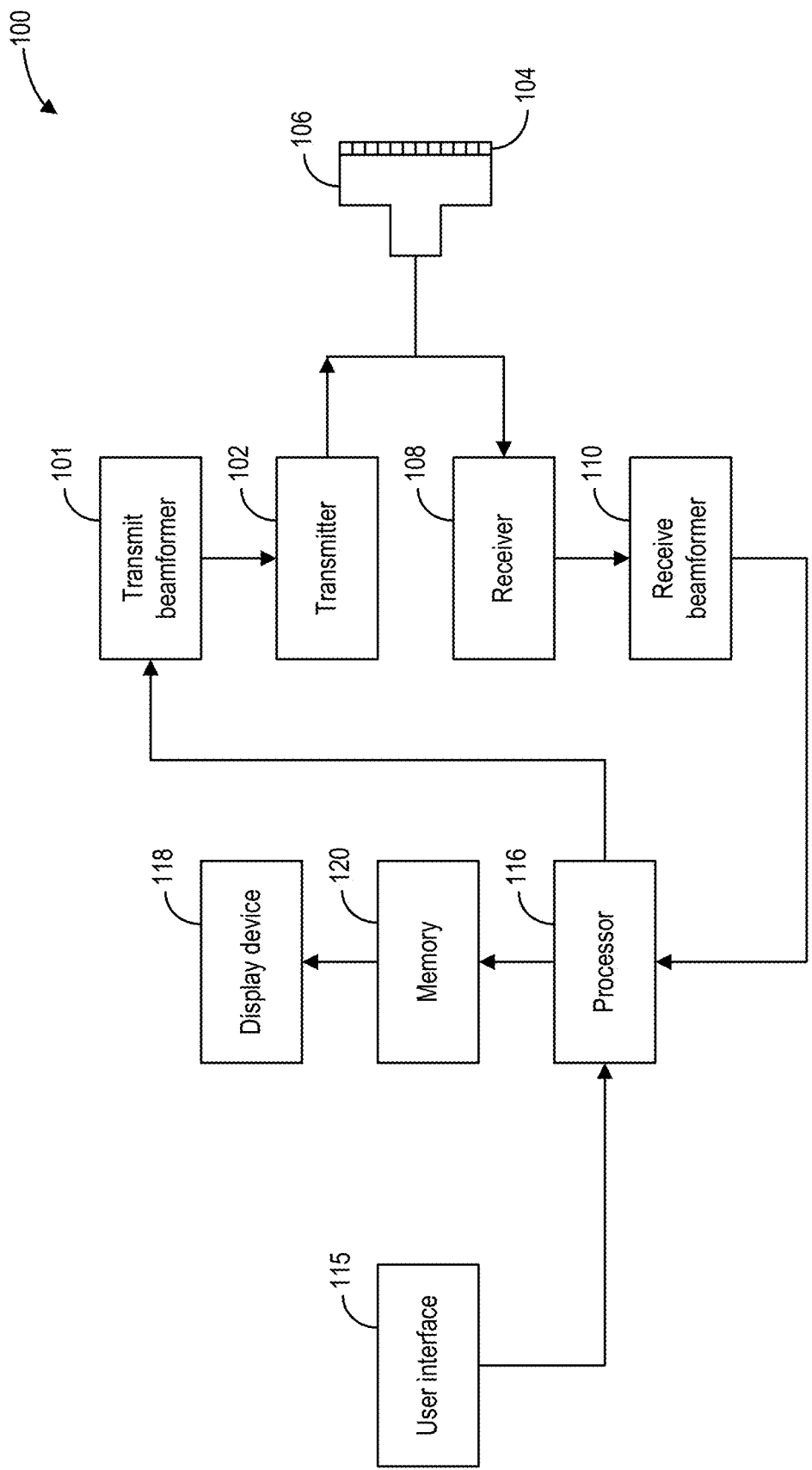
FIG. 1 shows an ultrasound system.

The following description relates to various embodiments of an ultrasound imaging device. The ultrasound imaging device may use pulse inversion during scanning routines. The pulse inversion may transmit two successive pulses in each direction at a single location comprising the scan, where each pulse includes an opposite waveform. The pulse inversion may be used in place of other imaging methods, such as harmonic imaging. A fundamental echo is linear with respect to a pulse amplitude, while a second harmonic pulse is quadratic with respect to the pulse amplitude. By transmitting the two pulses with opposite polarity the fundamental echo may be muted while enhancing the second harmonic pulse. By doing this, a large bandwidth may be used during transmission and reception since the fundamental components may be removed by the summation process. One drawback to transmitting two pulses of opposite polarity may include a reduced frame rate, that is to say, half a frame rate of single fire harmonics. Thus, a number of applications in which the two pulses are transmitted may be limited such as in high-framerate applications including multiplane acquisitions and in 3D setups.

The inventors recognize the above described drawbacks to transmitting two pulses and have come up with a way to at least partially solve them. In one example, a method for an ultrasound imaging system includes alternating a transmit beam pulse polarity for a plurality of laterally spaced transmit beams. In this way, a frame rate may be increased relative to transmitting two pulses of opposite polarity in the same direction at the same location.

In one example, a retrospectively focused secondary data set from a plurality of pulses comprises a "positive" polarity (e.g., a first waveform) may be collocated with a retrospectively focused secondary data set from a plurality of pulses that comprises a "negative" polarity (e.g., a second waveform, negating the first waveform). A summation of the plurality of positive and negative polarity pulses may be determined, which achieves a fundamental energy cancellation desired for accurate harmonic imaging.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. The modules or units shown in the attached figures may represent the hardware that operates based on software or hardwired instructions, the software that directs hardware to perform the operations, or a combination thereof.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound system 100 may be used to train a machine learning model. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processer 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data or 3D data of one or more planes at a significantly faster rate relative to the harmonic imaging of previous examples. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the disclosure may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a framerate of, for example, 60 Hz to 70 Hz (e.g., 60 to 70 frames per second) for 2D applications.

Images generated from the data may be refreshed at a similar frame-rate on display device 118. Other embodiments may acquire and display data at different rates. For example, some embodiments, such as a 3D application, may acquire data at a range of 15 to 30 Hz. It will be appreciated that other framerate values may be used without departing from the scope of the present disclosure.

A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present disclosure, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a three-dimensional or a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Figure 2A:
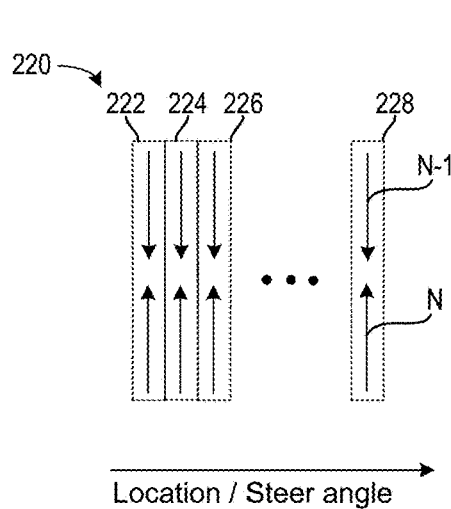
FIG. 2A shows a prior art example of a harmonic pulse scanning routine.

Turning to FIG. 2A, it shows a prior art example for a scan sequence 200 of a pulse inversion acquisition including a plurality of pulse sets 220 plotted against location/steer angle. A first pulse set 222 of the plurality of pulse sets 220 includes a first pulse and a second pulse. The second pulse may be a negated version (e.g., an opposite) of the first pulse. Herein the first pulse may be referred to as a positive polarity pulse and the second pulse may be referred to as a negative polarity pulse. The positive polarity pulse may have a given/desired waveform and the negative polarity pulse may have an inverse waveform of the waveform of the positive polarity pulse. The positive polarity pulse and the negative polarity pulse are transmitted at an identical location sequentially, wherein there is no lateral difference between locations at which the pulses are transmitted. That is to say, positive polarity pulse of the first pulse set 222 is fired at a first time at a first location and the negative polarity pulse of the first pulse set 222 is fired at a second time directly after the first time at the first location. The prior art may image in this way due to a fundamental echo being linear with respect to a pulse amplitude, while a second harmonic pulse is quadratic with respect to the pulse amplitude. Thus, the transmission of the positive and negative polarity pulses may lead to a cancelling of a fundamental spectrum component such that it is not included in a summation process. This may result in reduced noise and simpler corrections. It may also reduce a demand for removing fundamental energy by spectral filtering, allowing a larger bandwidth of received data that translates into higher resolution.

Following transmission of the first pulse set 222, a second pulse set 224 is transmitted, also including a positive polarity pulse and a negative polarity pulse at a second location, different than the first location. A third pulse set 226 may be transmitted following the second pulse set 224, the third pulse set 226 include a positive polarity pulse and a negative polarity pulse. The plurality of pulse sets 220 may continue to a final pulse set 228 such that a total number of positive pulses is equal to a total number of negative pulses. Each of the pulse sets fired in the prior art are at a fixed location, which may result in a reduced frame rate, decreasing an applicability of the harmonic imaging. In other words, two transmit pulses of a pulse set may be emitted for each transmit beam steering location, which lowers the framerate relative to other sequences that transmit a single pulse per steering location.

As illustrated in FIG. 2A, the positive and negative pulses within a given set are co-located. As such, time delays and other corrections factors to co-locate transmission may be avoided, which may simplify further calculations. However, as described above, the example of the prior art may be limited in a number of applications in which it may be used. For example, due to a lower framerate (e.g., half) of the previous example relative to single fire harmonic applications, its utility may be limited and it may not be executed during higher framerate applications.

Figure 2B:
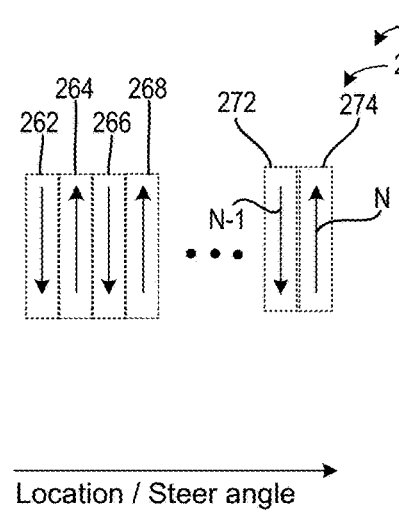
FIG. 2B shows a first embodiment of a harmonic pulse scanning routine according to the present disclosure.

Turning now to FIG. 2B, it shows a first embodiment 250 of a scan sequence for a pulse inversion scheme including a plurality of individual pulses 260 plotted against location/steer angle. A first pulse 262 may include only a negative polarity pulse. A second pulse 264, following the first pulse 262, may include only a positive polarity pulse. That is to say, the waveform of the first pulse 262 is opposite to the waveform of the second pulse 264, such that the waveforms of the first and second pulses are negations (e.g., opposites) of one another. In one example, a second location of the second pulse 264 is different than a first location of the first pulse 262. A third pulse 266, following the second pulse 264, may be a negative polarity pulse at a third location different than each of the first and second locations. A fourth pulse 268, following the third pulse 266, may be a positive polarity pulse at a fourth location different than each of the first through third locations. The individual pulses may continue until there is a number, N/2, of positive pulses ending at the Nth location 274 and a number, N/2, of negative pulses ending at the N-lth location 272. In this way, a number of positive pulses and a number of negative pulses is equal, each individual pulse being transmitted at unique locations.

Thus, the scan sequence of FIG. 2B fires each transmit beam with a single pulse where its polarity alternates from direction to direction at unique, laterally different locations, instead of repeating the same beam direction twice with two pulses of opposite polarity for each consecutive location in the grid, as shown in the prior art of FIG. 2A. The received data (e.g., the echoes resulting from the transmit pulses) may form two sparse grids, one for each of the positive and negative polarities. From the recorded data from each of the two sparse grids of equal polarity, a retrospectively focused secondary data set may be reconstructed at particular intermediate directions that are shared with the other sparse grid of opposite polarity. The retrospectively focused secondary data set from the pulse of positive polarity is thus co-located with the retrospectively focused secondary data set from the pulse of negative polarity and a traditional summation of echoes from these pulses may be performed thus achieving the fundamental energy cancellation used to perform desired harmonic imaging. Additional details about the generation of the retrospectively focused secondary data set are described below.

In one example, the embodiment of FIG. 2B includes a sparse set of positive data and a sparse set of negative data, since there was not a full transmit of positive or negative pulses, unlike the example of FIG. 2A. Analysis may then include interpolating data for the positive data set and interpolating data for the negative dataset to accommodate for the reduced amount of data. The interpolated data may be at co-located positions, so that they can be summed. Summing these secondary data sets may remove a fundamental echo while achieving an enhancement in harmonic imaging with an increased frame rate relative to the prior art. In one example, the frame rate of the example of FIG. 2B is about twice the frame rate of the prior art.

More specifically, an energy of the echoes includes a fundamental part that may depend linearly on pressure. The energy of the echoes may be inverted for opposite direction pulses. The energy of the echoes may further depend on a harmonic component equal to a square of the pressure, which is an equal value of the positive and negative pulse. By summing the echoes for the positive and negative pulses, only the harmonic component may remain, which may be the component used for cardiac imaging, for example.

Figure 3:
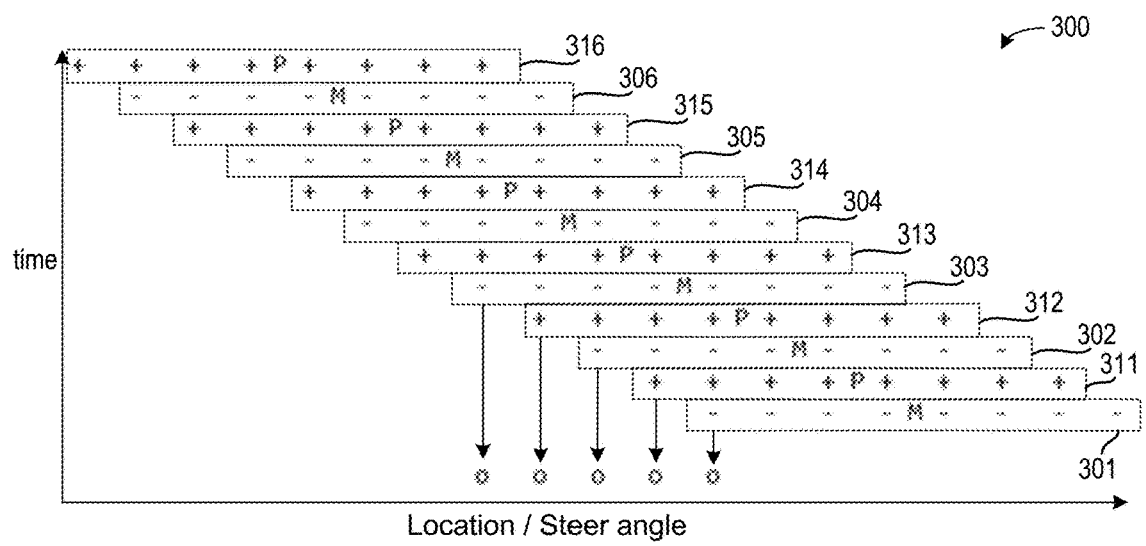
FIG. 3 shows a second embodiment of a harmonic pulse scanning routine.

Turning now to FIG. 3, it shows a second embodiment 300 of retrospective transmit beam processing including a single-stage RTB in an eight MLA grid with only one RTB output. Single-stage RTB may be configured to form an image directly from an element-domain received data measured for each transmit.

Sets of transmit beams for which the pulse polarity is positive may alternate with sets of transmit beams carrying negative pulse polarities. It should be noted that the term positive pulse and negative pulse implies that if the positive pulse is a first shape (e.g., a first waveform), the negative pulse is obtained by negating the first shape to produce a second waveform opposite the first waveform, as described above. A transmit beam may be defined as a pulse of a certain polarity along a direction. Herein the transmit beam including the positive pulse polarity may be referred to as a positive transmit beam and the transmit beam including the negative pulse polarity is referred to as a negative transmit beam. In one example, a total number of positive polarity pulse transmit beams is equal to a total number of negative polarity pulse transmit beams.

The "+" illustrate received MLA line locations of echoes from positive transmit beams (where the locations of the positive transmit beams are shown as P) and the "–" illustrate received MLA locations of echoes from negative transmit beams (where the locations of the negative transmit beams are shown as M. The horizontal axis illustrates a location/steer angle and the vertical axis illustrates time. In the example of FIG. 3, a first set 301 of transmitted negative beam echoes are received, followed by a second set 311 of received echoes from positive transmit beams. The received echoes from positive transmit beams alternate with echoes from negative transmit beams, such that a third set 302 follows the second set 311, a fourth set 312 follows the third set 302, a fifth set 303 follows the fourth set 312, a sixth set 313 follows the fifth set 303, a seventh set 304 followed the sixth set 313, an eighth set 314 follows the seventh set 304, a ninth set 305 follows the eighth set 314, a tenth set 315 follows the ninth set 305, an eleventh set 306 follows the tenth set 315, and a twelfth set 316 follows the eleventh set 306. Each set may include an equal number of transmit beams. For example, the first set 301 may include eight receive beams generated from echoes of the positive transmit beams and the second set 311 may include eight negative pulse receive beams generated from echoes of the negative transmit beams. As such, each of the sets from the first through the twelfth includes eight receive beams with a total number of positive receive beams being equal to a total number of negative receive beams. Additionally, each beam direction is fired individually only once (e.g., single fire), with either a positive or a negative pulse polarity, such that a frame rate is increased relative to the example of FIG. 2A.

A summation at each location is performed to produce pulse inverted RTB output lines, which are illustrated via arrows where the positive and negative receive beams are summed equal to zero. Thus, in the second embodiment, there may be a balance in the weighting of positive and negative pulse contributions. That is to say, the pulse contributions are selected such that the weighted sum of the positive pulses and the negative pulses is zero. In this way, an image accuracy may be enhanced. One technical effect of the embodiment of FIG. 3 is to increase a frame rate of a RTB procedure with pulse inversion relative to the prior art, allowing a suppression in fundamental energy and thus allowing a larger receive bandwidth typical of pulse inversion at minimal framerate penalty The embodiment 300 may enhance a scanning procedure for 3D and 2D scanning.

Figure 4:
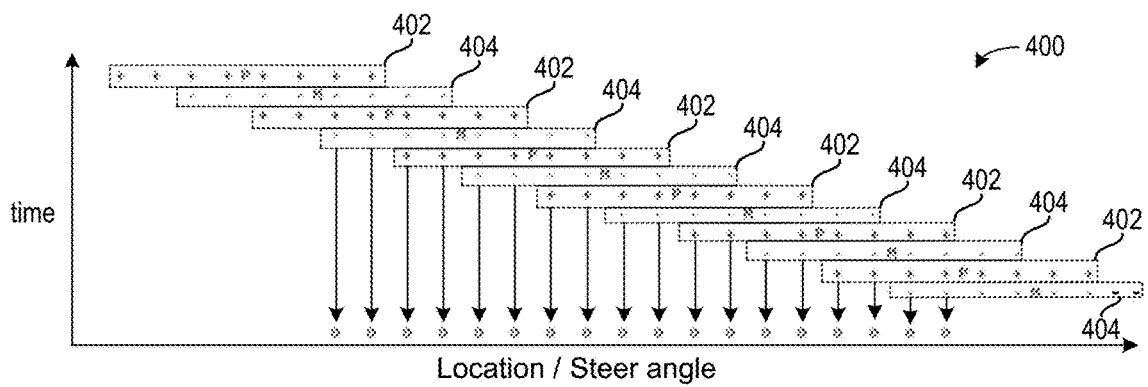
FIG. 4 shows a third embodiment of a harmonic pulse scanning routine.

Turning to FIG. 4, it shows a third embodiment 400 including a dual RTB output from an eight MLA grid. Dual or other multiple output RTB may be an alternative to single output RTB lines that may reduce a number of vectors to be transferred from a front-end to a receive beamformer (e.g., beamformer 101 of FIG. 1). The third embodiment 400 may include a single-stage RTB similar to the second embodiment 300 of FIG. 3. In one example of dual RTB systems, the RTB system spaces the receive-beamformed lines widely enough to facilitate a combination thereof. Thus, if received lines are to be combined, then the different transmits may at least somewhat overlap.

In one example, the embodiment 400 of FIG. 4 may be similar to the embodiment 300 of FIG. 3 except that a number of reconstructed beam output locations per transmit beam is different. The difference may be based on a layout selected with respect to a degree of overlap between beams, and therefore a number of generated output beams. The embodiment 400 may include a framerate higher than that of embodiment 300 of FIG. 3 due to a number of transmit beams to cover a scan area being smaller due to the reduced overlap of embodiment 400 relative to embodiment 300. In one example, if the receive beam distances between embodiments 300 and 400 are equal, then transmit beams of the embodiment 400 may be broader than transmit beams of the embodiment 300. In this way, a threshold distance between adjacent locations may be increased in the example of FIG. 4 relative to the example of FIG. 3. In one example, the threshold distance is a non-zero, positive number based on a desired frame rate, image quality, or the like.

In the third embodiment 400, sets of received echoes from alternating polarity transmit beam sets are illustrated, wherein the sets include positive polarity receive beams 402 and negative polarity receive beams 404. The positive and negative pulse polarity beams alternate as described above with a total amount of positive receive beam energy (echoes) being equal to a total amount of negative receive echo energy.

In this example, each RTB sum comprises two positive pulse echoes and two negative pulse echoes, which are represented by arrows pointing to a sum of 0 fundamental energy. In the example of FIG. 4, it may be challenging to obtain an equal sum for negative and positive transmits. A first method of achieving the equal sum is to force the weights into the RTB sum to be equal for the two outermost MLAs of each beam on each side, and for the two innermost MLAs on each beam on each side so that each MLA component with unique tx-rx distance is weighted in with the same amount for positive and negative polarities. More specifically, two outer MLAs of the first set of positive polarity beams 402 and the last set of negative polarity beams are used along with four MLAs from the positive and negative polarity beams therebetween.

Figure 5:
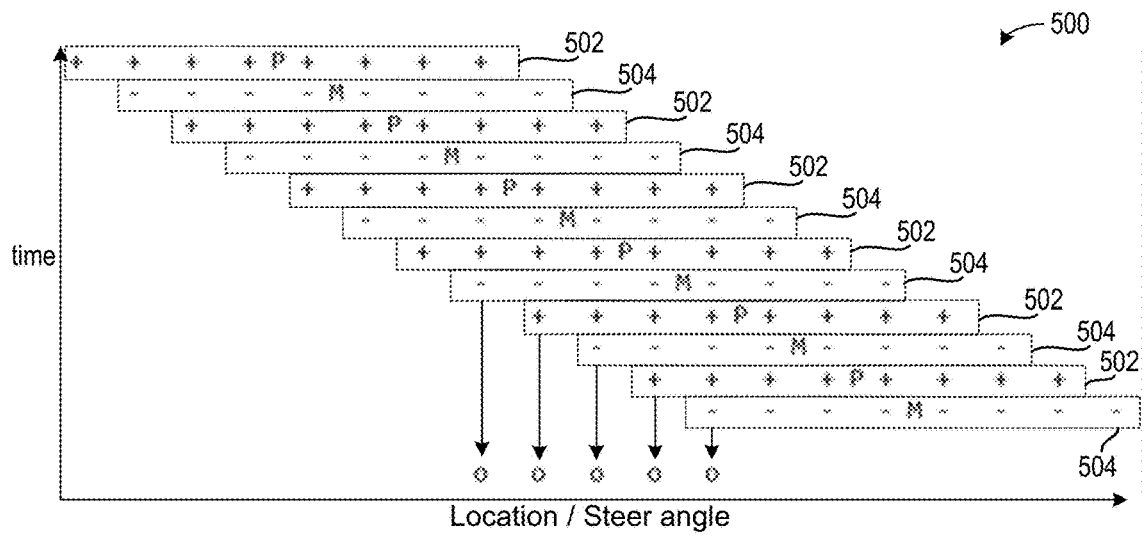
FIG. 5 shows a fourth embodiment of a harmonic pulse scanning routine.

FIG. 5 shows a fourth embodiment 500 of a set of successive receive beams of alternating polarity, including sets of positive polarity receive beams 502 and sets of negative polarity receive beams 504. The "+" and "−" signs refer to intended future receive beamforming locations (see FIG. 6), but the data are illustrated as channel data sets in the example of FIG. 5.

The transmits within the channel data sets are only locations intended for beamforming, resulting in different locations for the receive beams. The channel data sets may be split into positive events P and negative events M, where RTB correction delays and beamforming delays may be performed to the data sets suitable for the requested locations marked by "+" and "−", as shown in FIG. 6.

Figure 6:
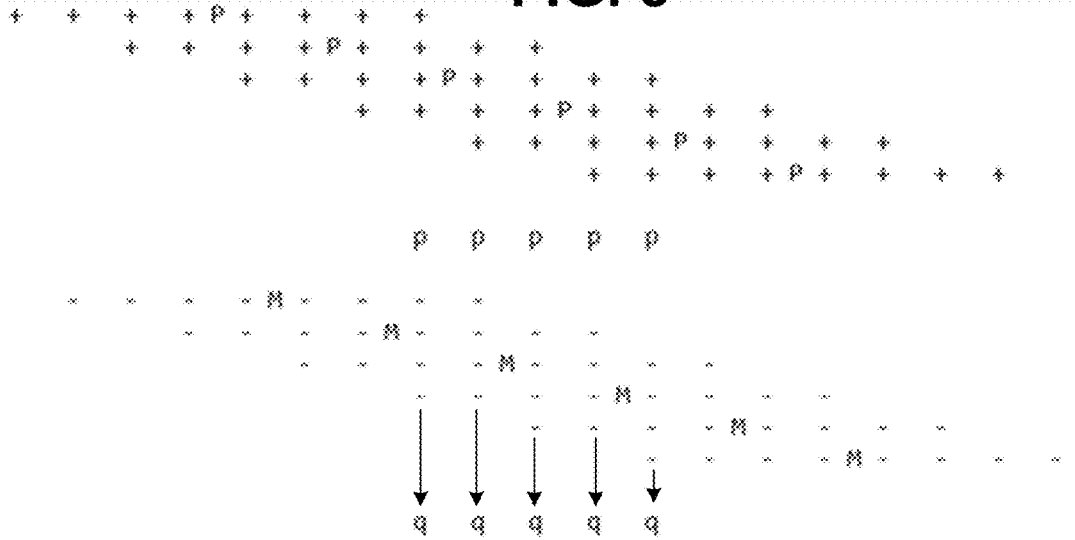
FIG. 6 shows a fifth embodiment of a harmonic pulse scanning routine.

Turning to FIG. 6, it shows an embodiment 600 of the channel data sets of FIG. 5 separated into positive and negative event data sets. The negative "M" events may be gathered and subjected to beamforming delays desired for a receive location and RTB delays to correct for transmit wave front registration delay at the receive location.

FIG. 6 shows an example of two stage RTB, which includes where the first stage RTB on channel data retains the data as channel data when the positive and negative pulses are summed, thus there exists a channel data set devoid of fundamental energy that can be used with non-linear beamforming techniques such as coherence factors, while working on data without fundamental clutter.

The first stage then does RTB on the channel data, compensating the echoes for the transmit wavefront delays at directions on the collocated grid shared by positive and negative pulse beams and combining beams of the same pulse polarity onto synthetic channel data at the collocated grid locations, for both negative and positive pulses. When these channel data (of positive and negative pulse echoes corrected to the same directions in space) are summed, the resulting synthetic channel data set is devoid of fundamental energy. This data can then be used in regular beamforming or in non-linear beamforming techniques while also being used in a second stage RTB in a plurality of MLA directions.

The system, via the processor 116 instructions stored on memory 120 of FIG. 1, may execute the summation of the delay corrected channel data of positive and negative amplitude to perform the pulse inversion operation on the channel data with a desired number of receive beams. In this way, positive and negative transmit energies that are co-located are summed, as shown by arrows leading to values of zero fundamental energy. Additionally or alternatively, nonlinear operations, including coherence estimates, may be included on channel data devoid of fundamental energy. While these steps may demand increased buffering of different pre-corrected channel data sets to retain the positive and negative versions of channel data representative of every output location, the steps may provide the non-beamformed pulse inverted channel data summed together to be devoid of fundamental energy, thus enabling non-linear beamforming methods on only harmonic channel data.

This may be accomplished by a performing a receive beamforming with a MLA on an element data as a pre-processing step. It will be appreciated that as long as a number of receives lines produced per transmit is smaller than a number of array elements, the amount of data is reduced (e.g., beamformed data can also be sampled at a lower rate than element data). The advantage of the example of FIG. 6 is that channel data may be available that are devoid of fundamental energy due to the positive and negative pulse beam echoes being prepared without performing the beam sum and can be summed together to produce a channel data set with more clear harmonics signal contents to which non-linear beamforming techniques can be applied.

Thus, in one example, FIG. 6 shows another method for performing the retrospective transmit beams on the channel data from a sparse grid of each of the polarities independently prior to regular beamforming, thus preparing a synthesized channel data set from each of the pulse polarities that are aligned as if recorded with transmit beams at a synthetic co-incidental location grid identical to a beamforming rx-grid described with respect to the first method. This is to say, a first synthesized channel data set may include only positive pulse polarities that are transmitted to be combined and a second synthesized channel data set may include only negative pulse polarities that are transmitted to be combined (e.g., overlapping with positive pulse polarities where a sum is equal to zero). The resulting synthetic channel data sets for positive polarity and negative polarity can then be summed to form a pulse inversion on the channel data and these data, now devoid of fundamental energy and RTB corrected, may then be subjected to beamforming Turning to FIG. 7, it shows an embodiment 700 of an example interpolation of a channel data between two events of equal polarity onto two new synthetic locations distanced ¼ and ¾ of the spacing between the two positive events. Said another way, an original data set 702 is split into positive and negative transmits. The negative polarity channel data is interpolated and then the positive polarity channel data is interpolated. By doing this, the beam locations for the negative and the positive polarity sets may now overlap via the new negative and positive synthetic locations, 704, 706, respectively, described above. The resulting channel data can thus be summed together to perform the pulse inversion operation 708 on channel data. Subsequent data, now devoid of fundamental content, can enter into e.g. regular beamforming and retrospective beamforming. This example may experience a lack of desired transmit wave front alignment of the combined events. Additionally, unless beam-to-beam distance is relatively small thereby increasing an accuracy of the phase interpolation assumption, the embodiment 700 may generate artifacts in the subsequent imaging processing. The artifacts, which may be motion artifacts, may be generated due to the interpolation being between two datasets acquired at different time points in which an imaged medium may move between the different time points. One advantage of the example of FIG. 7 is a relatively simple implementation on channel data level and with the low vulnerability to motion artifacts lying in the combination of only temporally close events.

Figure 7:
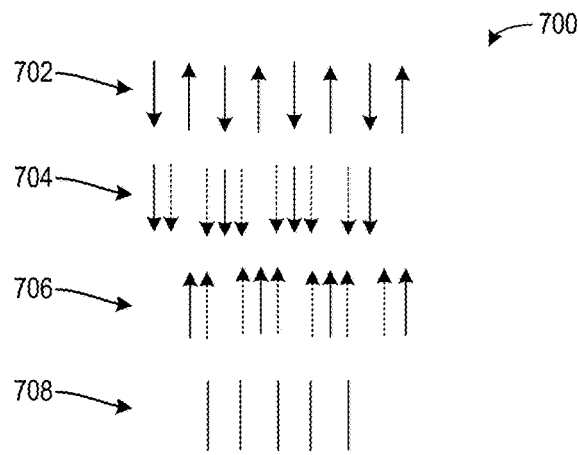
FIG. 7 shows a diagram for processing ultrasound data gathered from the harmonic pulse scanning routine.

The embodiment of FIG. 7, which shows interpolation of channel data without delay compensation may rely only on phase interpolation to correct for a difference in tx beam direction. This may result in a less accurate approximation than the RTB approach in the previous embodiments. However, the embodiment of FIG. 7 may be executed with a low computational complexity since after the synthetic channel data is generated from simple interpolation of channel data, all subsequent beamforming may be performed as-is. The memory usage of this is less than the two-stage RTB alternative of FIG. 6. Furthermore, since this method only combines data from pairs of neighboring beams of the same polarity for reconstructing the co-linear positive and negative pulse events, the summation of these and hence the rejection of fundamental energy is less effected by motion.

Said another way, the channel data divided by the sets of positive beams and the sets of negative beams. Interpolate internally in each data set between neighboring transmit beams of same polarity forming synthetic data at a coincidental grid. Then sum the two polarities to achieve pulse inverted channel data set that can be entered into subsequent beamforming, such as nonlinear beamforming methods, regular beamforming and/or RTB.

One embodiment for firing transmit beams at different locations with different waveforms may include combining alternating co-located receive echoes from alternating polarity pulse transmissions in different adjacent directions. The embodiment may further include compensating the recorded echoes for difference in wavefront arrival times and performing a weighted sum of the co-located delay-corrected data from several transmit directions of similar polarity in order to achieve a retrospectively focused echo signal at each location (in a common grid) of a certain polarity. The embodiment may further include summing together the synthesized co-located echo data for the positive and the negative pulses in order to remove fundamental energy, either as a separate stage or as integrated in the previous step.

A further embodiment for firing transmit beams at different locations with different waveforms may include performing the retrospective transmit beamforming operation with a delay and sum on channel data without actually summing the channel data, thus producing a channel data set where positive and negative pulse echoes have been aligned and summed, that can be subsequently used as input to regular beamforming, non-linear beamforming methods, and/or a second stage RTB.

An additional embodiment for firing transmit beams at different locations with different waveforms may include where the channel data synthesized are generated using IQ interpolation of neighboring pairs of channel data from pulses of same polarity onto a grid shared with the opposite polarity, then summing the channel data from the opposite polarities and performing subsequent regular beamforming, non-linear beamforming methods and/or RTB. This embodiment may be less accurate than the previous two while using the least amount of computational power.

Figure 8:
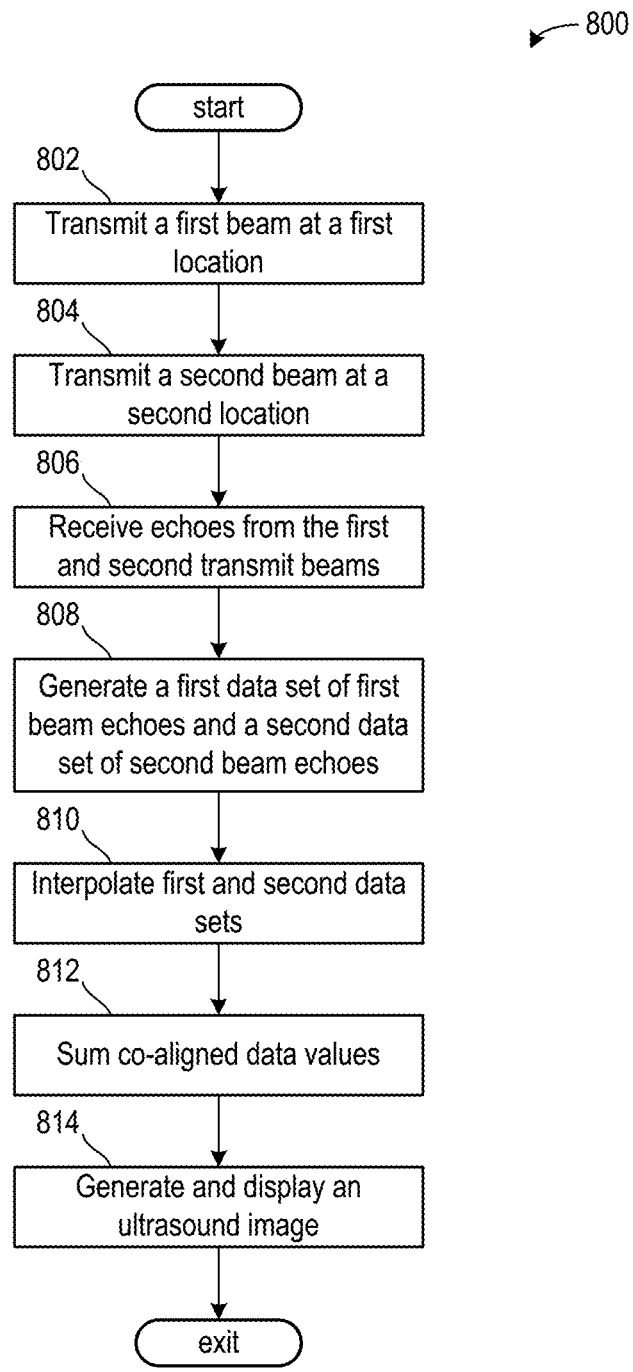
FIG. 8 shows a method for processing ultrasound data.

Turning to FIG. 8, it shows a method 800 for retrospective transmit beam (RTB) processing. Instructions for carrying out method 800 may be executed by a controller (e.g., processor 116 of FIG. 1) based on instructions stored on a memory of the controller and in conjunction with signals received from sensors of the imaging system, such as the sensors described above with reference to FIG. 1. The controller may adjust a display of the imaging system according to the method described below.

The method 800 begins at 802, which includes transmitting a first beam at a first location. Transmitting the first beam may include a transmit beamformer (e.g., transmit beamformer 101 of FIG. 1) and a transmitter (e.g., transmitter 102 of FIG. 1) driving transducer elements (e.g., transducer elements 104 of a probe 106 of FIG. 1) toward an imaging medium. In some examples, additionally or alternatively, the first beam may be one of a plurality of first beams, wherein the plurality of first beams may be fired sequentially, each at disparate locations. In one example, each of the plurality of first beams is a positive transmit beam.

The method 800 may proceed to 804, which includes transmitting a second beam at a second location. Transmitting the second beam may include the transmit beamformer and the transmitter driving the transducer elements toward the imaging medium. The second beam may be a transmit beam with a waveform opposite to (e.g., negating) a waveform of the first transmit beam. The second beam may be transmitted between neighboring first beams or may be transmitted following the plurality of first beams. In one example, the second beam may be a plurality of second beams, wherein a number of second beams in the plurality of second beams is equal to the plurality of first beams. Additionally or alternatively, the plurality of first beams may be interleaved with the plurality of second beams such that adjacent first beams are interrupted by a second beam.

The method 800 may proceed to 806, which includes receiving echoes from the first and second transmit beams. Receiving the echoes may include where the echoes are converted into electrical signals, or ultrasound data, by the transducer elements and the electrical signals are received by a receiver (e.g., receiver 108 of FIG. 1). The electrical signals representing the received echoes are passed through a receive beamformer (e.g., receive beamformer 110 of FIG. 1) that outputs ultrasound data to the controller.

The method 800 may proceed to 808, which includes generating a first data acquisition set of first beam echoes and a second data acquisition set of second beam echoes. The first data set of first beam echoes and the second data set of second beam echoes.

The method 800 may proceed to 810, which includes interpolating the first data acquisition set and the second data acquisition set via weights and delays. The delays may be based on a difference in wavefront arrival times. The weights may be based on a weights sum of co-located delay corrected data from several transmit directions of similar polarity (e.g., first beams or second beams).

The method 800 may proceed to 812, which includes summing co-aligned data values of the first and second data acquisition sets. By summing the co-aligned data values, fundamental energy of the transmit beams may be cancelled. By doing this, only a harmonic component may remain.

The method 800 may proceed to 814, which includes generate and display an ultrasound image.

In one example, conditions for reconstructing the co-located signal with both polarities to be obtained in an entirety in the region of interest (ROI), then either the transmit beam may be broadened or the beam layout may be increased in density to ensure some overlap between the closest transmit beams of same polarity also around the focus depth where the beam is at its narrowest. Or the focal region may be shifted out of the ROI. There is thus a tradeoff may prevent a complete doubling of the framerate, relative to the example of FIG. 2A, since the beam sampling around the focal region may be denser, or other aspects of image quality related to two-way focusing strength may be adjusted, which decreases the framerate. At any rate, the framerate of the scanning method of FIG. 8 and of the embodiments of FIGS. 2B through 7 is increased relative to the prior art example of FIG. 2A.

FIG. 9 shows a data set 900 recorded with the embodiment 250 of FIG. 2B. A single fire beam layout where every alternate transmit beam is fired with the opposite polarity pulse. Regular RTB is then performed on these data effectively reconstructing RTB output lines and summing negative and positive pulses in the same operation out-of-the-box. The same spacing and thus framerate (70 fps) as the corresponding single fire harmonic setup is used and there is little clutter in the image and no clear artefacts are seen.

FIGS. 10A and 10B show two frames in a loop where while scanning the same target, the pulse polarity on every alternate transmit beam direction was reversed, retaining the framerate and every other setup parameter. The bandwidth used was relatively high to include fundamental energy and the pulse used was a broad band type of two half periods.

FIG. 10A illustrates an embodiment 1000 of the prior art where a receive bandwidth is increased to an extent where the single fire harmonic using the same pulse has been contaminated with fundamental energy showing up as a relatively large clutter in the image. FIG. 10B shows an embodiment 1050 where scanning conditions are changed to use an opposite polarity pulse on every alternate transmit beam, all else being equal. As shown, the image quality of FIG. 10B is greater than the image quality of FIG. 10A, with fundamental contents of the image being removed along with reduced haze and clutter.

In this way, novel pulse inversion harmonics may be performed without reducing the framerate by doing single fires with alternating polarity on each beam. Retrospective transmit techniques may be used reconstruct aligned data of positive and negative events. The technical effect of the pulse inversion harmonics with alternating polarity on each beam or each beam set is to increase a framerate of the imaging for enhanced imaging during 3D image acquisition or the like.

An embodiment of a method for ultrasound imaging, the method comprises transmitting a first beam with a first waveform at a first location and a second beam with a second waveform at a second location via an ultrasound probe, wherein the second location is different than the first location and the second waveform is different than the first waveform. A first example of the method further includes transmitting comprises transmitting the second beam subsequent to the first beam, and wherein the second location is laterally different than the first location. A second example of the method, optionally including the first example, further includes where the second beam waveform is a negation of the waveform of the first beam. A third example of the method, optionally including one or more of the previous examples, further includes where the first beam is one of a plurality of first beams and the second beam is one of a plurality of second beams. A fourth example of the method, optionally including one or more of the previous examples, further includes gathering a first data acquisition set comprising only echoes of the plurality of first beams and a second data acquisition set comprising only echoes of the plurality of second beams. A fifth example of the method, optionally including one or more of the previous examples, further includes summing and delaying a first portion of data and a second portion of data to form a first acquisition output. A sixth example of the method, optionally including one or more of the previous examples, further includes summing includes summing co-aligned values of the first and second data acquisition sets to remove a fundamental energy. A seventh example of the method, optionally including one or more of the previous examples, further includes interpolating the first data acquisition set and the second data acquisition set onto new locations distanced a threshold amount from an original location. An eighth example of the method, optionally including one or more of the previous examples, further includes summing aligned positive and negative transmits following the interpolating. A ninth example of the method, optionally including one or more of the previous examples, further includes where the first beam has a first waveform and the second beam has a second waveform, the second waveform being an inverse of the first waveform, and wherein the first location and the second location are locations of a plurality of locations, wherein each of the plurality of locations receives only the first beam or the second beam.

An embodiment of an ultrasound system, comprises a probe configured to transmit beams and acquire ultrasound data, and a processor comprising computer-readable instructions stored on non-transitory memory thereof that when executed enable the controller to alternate firing of positive pulse transmit beams and negative pulse transmit beams at different locations. A first example of the ultrasound system, further includes where the instructions further enable the controller to fire a plurality of positive transmit beams along a first plurality of locations and a plurality of interleaved negative transmit beams along a second plurality of locations, wherein a number of the plurality of positive transmit beams is equal to a number of the plurality of negative transmit beams. A second example of the ultrasound system, optionally including the first example, further includes where locations within the first plurality of locations are different from one another and from locations within the second plurality of locations. A third example of the ultrasound system, optionally including one or more of the previous examples, further includes where the instructions further enable the controller to process acquired ultrasound data and co-locate positive and negative transmit beams. A fourth example of the ultrasound system, optionally including one or more of the previous examples, further includes where the instructions further enable the controller to determine a number of transmit events to combine, wherein a sum of combined transmit events is equal to zero.

An embodiment of a method for an ultrasound system comprising a processor configured to execute the method, the processor communicatively coupled to an ultrasound probe via a transmitter, wherein the ultrasound probe provides feedback to the processor via a receive beamformer, the method, comprises generating a plurality of ultrasound transmit pulses, each transmit pulse positioned at a unique transmit beam location, where the plurality of ultrasound transmit pulses are generated with alternating positive polarity and negative polarity, receiving echoes from the plurality of ultrasound transmit pulses, and generating an ultrasound image from the received echoes, including summing location-aligned data of the received echoes from positive polarity transmit pulses and negative polarity transmit pulses. A first example of the method further includes where generating the plurality of ultrasound transmit pulses comprises generating a first transmit pulse having a positive polarity at a first transmit beam location and generating a subsequent, second transmit pulse having a negative polarity at a second transmit beam location, wherein the first transmit pulse including a positive polarity includes the first transmit pulse having a first waveform and wherein the second transmit pulse having a negative polarity includes the second transmit pulse having a second waveform that is inverse of the first waveform. A second example of the method, optionally including the first example, further includes generating a first data set of first beam echoes and a second data set of second beam echoes following receiving the echoes. A third example of the method, optionally including one or more of the previous examples, further includes interpolating the first data set and the second data set via weights and delays, wherein the delays are based on a difference in wavefront arrival times, and wherein the weights are based on a weights sum of co-located delay corrected data from several transmit directions of similar polarity. A fourth example of the method, optionally including one or more of the previous examples, further includes where synthetically co-aligning the first data set of first beam echoes and the second data set of the second beam echoes.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for ultrasound imaging, the method comprising:
    transmitting, via an ultrasound probe, a plurality of beams toward an imaging subject according to a pulse-inversion scheme, the plurality of beams including a first beam with only a single pulse of a first polarity transmitted at a first steer angle and a subsequent second beam with only a single pulse of a second, opposite polarity transmitted at a second steer angle, wherein the second steer angle is different than the first steer angle, wherein each beam of the plurality of beams is transmitted at a different steer angle, and wherein the first beam is one of a plurality of first beams of the plurality of beams, each first beam having the first polarity, and the second beam is one of a plurality of second beams of the plurality of beams, each second beam having the second polarity; and
    generating an ultrasound image of the imaging subject from echoes of the plurality of beams received at the ultrasound probe, including applying retrospective transmit techniques to reconstruct aligned data resulting from the plurality of first beams and the plurality of second beams and summing the aligned data to cancel a fundamental spectrum component.

2. The method of claim 1, wherein remaining beams of the plurality of beams transmitted subsequent to the first beam and the second beam each include only a single pulse of either the first polarity or the second polarity, with pulses of the first polarity alternating with pulses of the second polarity.

3. The method of claim 1, wherein applying retrospective transmit techniques to reconstruct aligned data resulting from the plurality of first beams and the plurality of second beams and summing the aligned data to cancel the fundamental spectrum component comprises gathering a plurality of channel data sets, each channel data set formed from echoes produced as a result of a respective beam of the plurality of beams such that the plurality of channel data sets comprises sets of first polarity channel data and sets of second polarity channel data, splitting the plurality of channel data sets into a first data acquisition set comprising the sets of first polarity channel data and a second data acquisition set comprising the sets of second polarity channel data.

4. The method of claim 1, wherein applying retrospective transmit techniques to reconstruct aligned data resulting from the plurality of first beams and the plurality of second beams and summing the aligned data to cancel the fundamental spectrum component comprises generating a plurality of retrospective transmit beamforming (RTB) output lines, each RTB output line formed by summing co-located receive multi-line acquisition (MLA) lines, and wherein each respective MLA line is formed from echoes produced as a result of a respective beam of the plurality of beams.

5. The method of claim 3, further comprising retrospectively focusing, by adding beamforming delays, the first data acquisition set to form a secondary dataset of the first polarity on a first grid comprising a first plurality of locations, retrospectively focusing, by adding beamforming delays, the second data acquisition set to form a secondary dataset of the second polarity on a second grid comprising a second plurality of locations collocated with the first plurality of locations, and summing the secondary dataset of the first polarity and the secondary dataset of the second polarity, and wherein the ultrasound image is generated from the summed secondary datasets after beamforming.

6. The method of claim 4, wherein summing the co-located receive MLA lines comprises forcing weights into each RTB output line to be equal for two outermost MLAs of each beam on each side, and for two innermost MLAs on each beam on each side, so that each MLA component with unique transmit-receive distance is weighted in with the same amount for the first and second polarities.

7. The method of claim 5, further comprising summing co-aligned channel data sets of the first and second data acquisition sets to remove a fundamental energy, and wherein generating the ultrasound image comprises generating the ultrasound image from the summed co-aligned channel data sets.

8. The method of claim 7, further comprising interpolating between every two sets of first polarity channel data of the first data acquisition set and interpolating between every two sets of second polarity channel data of the second data acquisition set such that the interpolated first data acquisition set and the interpolated second data acquisition set comprise the co-aligned channel data sets.

9. The method of claim 8, wherein the interpolating is performed before the summing, and further comprising beamforming the summed co-aligned channel data sets to generate the ultrasound image.

10. The method of claim 1, wherein the plurality of beams is transmitted at a plurality of steer angles, wherein each respective beam is transmitted at one steering angle of the plurality of steer angles, and wherein a single beam is transmitted at each steer angle.

11. An ultrasound system, comprising:
 a probe configured to transmit a plurality of beams and acquire ultrasound data, the probe configured to transmit the plurality of beams toward an imaging subject according to a pulse-inversion scheme, the plurality of beams including a first beam with only a single pulse of a first polarity transmitted at a first steer angle and a subsequent second beam with only a single pulse of a second, opposite polarity transmitted at a second steer angle, wherein the second steer angle is different than the first steer angle, wherein each beam of the plurality of beams is transmitted at a different steer angle, and wherein the first beam is one of a plurality of first beams of the plurality of beams, each first beam having the first polarity, and the second beam is one of a plurality of second beams of the plurality of beams, each second beam having the second polarity; and
 a processor comprising computer-readable instructions stored on non-transitory memory thereof that when executed enable the controller to:
  generate an ultrasound image of the imaging subject from echoes of the plurality of beams received at the probe, including applying retrospective transmit techniques to reconstruct aligned data resulting from the plurality of first beams and the plurality of second beams and summing the aligned data to cancel a fundamental spectrum component.

12. The ultrasound system of claim 11, wherein remaining beams of the plurality of beams transmitted subsequent to the first beam and the second beam each include only a single pulse of either the first polarity or the second polarity, with pulses of the first polarity alternating with pulses of the second polarity.

13. The ultrasound system of claim 11, wherein the plurality of beams is transmitted at a plurality of steer angles, wherein each respective beam is transmitted at one steering angle of the plurality of steer angles, and wherein a single beam is transmitted at each steer angle.

14. The ultrasound system of claim 11, wherein applying retrospective transmit techniques to reconstruct aligned data resulting from the plurality of first beams and the plurality of second beams and summing the aligned data to cancel the fundamental spectrum component comprises generating a plurality of retrospective transmit beamforming (RTB) output lines, each RTB output line formed by summing co-located receive multi-line acquisition (MLA) lines, and wherein each respective MLA line is formed from echoes produced as a result of a respective beam of the plurality of beams.

15. The ultrasound system of claim 14, wherein summing the co-located receive MLA lines comprises forcing weights into each RTB output line to be equal for two outermost MLAs of each beam on each side, and for two innermost MLAs on each beam on each side, so that each MLA component with unique transmit-receive distance is weighted in with the same amount for the first and second polarities.

\* \* \* \* \*